(12) United States Patent
Mann

(10) Patent No.: US 8,965,711 B2
(45) Date of Patent: *Feb. 24, 2015

(54) METHOD AND SYSTEM FOR DETERMINING THE ACCURACY OF DNA BASE IDENTIFICATIONS

(71) Applicant: Illumina, Inc., San Diego, CA (US)

(72) Inventor: Tobias Mann, Carlsbad, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/760,810

(22) Filed: Feb. 6, 2013

(65) Prior Publication Data

US 2013/0151446 A1 Jun. 13, 2013

Related U.S. Application Data

(63) Continuation of application No. 12/565,341, filed on Sep. 23, 2009, now Pat. No. 8,392,126.

(60) Provisional application No. 61/102,719, filed on Oct. 3, 2008.

(51) Int. Cl.
*G01N 33/48* (2006.01)
*G06N 99/00* (2010.01)
*G06F 19/22* (2011.01)
*G06F 19/24* (2011.01)

(52) U.S. Cl.
CPC .............. *G06N 99/005* (2013.01); *G06F 19/22* (2013.01); *G06F 19/24* (2013.01)
USPC .......................................................... 702/20

(58) Field of Classification Search
USPC .......................................................... 702/20
See application file for complete search history.

(56) References Cited

U.S. PATENT DOCUMENTS

| 5,302,509 A | 4/1994 | Cheeseman |
| 5,547,839 A | 8/1996 | Dower et al. |
| 6,236,944 B1 | 5/2001 | Miller et al. |
| 6,681,186 B1 | 1/2004 | Denisov et al. |

FOREIGN PATENT DOCUMENTS

WO 93/21340 10/1993

OTHER PUBLICATIONS

International Search Report and Written Opinion dated Dec. 17, 2009 for International Application No. PCT/US2009/058099, Filed Sep. 23, 2009.
Ewing, et al., "Base-Calling of Automated Sequencer Traces Using Phred. I. Accuracy Assessment", Genome Research, 8, 1998, 175-185.
Ewing, et al., "Base-calling of automated sequencer traces using phred. II. Error probabilities", Genome Research, 8, 1998, 186-194.
Giddings, et al., "A Software System for Data Analysis in Automated DNA Sequencing", Genome Research, 8, 1998, 644-665.

*Primary Examiner* — Jerry Lin
(74) *Attorney, Agent, or Firm* — Victor Huang; Illumina, Inc.

(57) ABSTRACT

A system for determining the quality of predicted DNA base identifications is disclosed, the system comprising a processor configured to receive a training data set, the training data set comprising a plurality of predicted DNA base identifications, define a group of subsets, compare the predicted DNA base identifications with actual DNA base identifications for training data within each subset of the group, determine a sampling characteristic for each subset of the group based on training data within the respective subset, and determine a quality characterization for predicted DNA base identifications within at least one of subset of the group based on the comparison and determined sampling characteristic, wherein the sampling characteristic comprises a confidence value comprising a binomial proportion confidence interval value.

19 Claims, 8 Drawing Sheets

METHOD AND SYSTEM FOR DETERMINING THE ACCURACY OF DNA BASE IDENTIFICATIONS

CROSS-REFERENCE TO RELATED APPLICATION

This application is a continuation of U.S. Utility application Ser. No. 12/565,341, filed on Sep. 23, 2009, which claims the benefit of U.S. Provisional Application No. 61/102,719, filed Oct. 3, 2008, the contents of each of which are hereby incorporated by reference in their entirety.

BACKGROUND OF THE INVENTION

1. Field of the Invention

Embodiments disclosed herein relate to a method and system for determining the accuracy of DNA base identifications, based at least partly on sampling characteristics of subsets within training data sets.

2. Description of the Related Art

With the progress of the Human Genome Project and its massive undertaking to sequence the entire human genome, researchers have been turning to automated DNA sequencers to process vast amounts of DNA sequence information. DNA, or deoxyribonucleic acid, is one of the most important information-carrying molecules in cells. DNA is composed of four different types of monomers, called nucleotides, which are in turn composed of bases linked with a sugar and a phosphate group. The four bases are adenine (A), cytosine (C), guanine (G), and thymine (T). The original state of a DNA fragment is a double helix of two antiparallel chains with complementary nucleotide sequences. The coded information of a DNA sequence is determined by the order of the four bases in either of these chains. This sequence of bases is often referred to as the nucleotide sequence or nucleic acid sequence of the DNA. Several chemical methods have been developed for detecting and identifying the bases in order, and such methods can be performed on automated equipment. However, the reliability of such base predictions may be limited by the performance of the equipment and the particular chemistry being used. Moreover, the accuracy of determining, or "calling" a base may vary between separate sequencing experiments, or even from base to base. Thus, there is a need for predicting the bases with a DNA sequence and assessing a quality measure associated with the prediction.

SUMMARY OF THE INVENTION

One embodiment is a method for predicting the accuracy of DNA base identifications. The method includes receiving a training data set, the training data set comprising a plurality of predicted DNA base identifications; defining a group of subsets; comparing the predicted DNA base identifications with actual DNA base identifications for training data within each subset of the group; determining a sampling characteristic for each subset of the group based on training data within the respective subset; and determining quality characterization for predicted DNA base identifications within at least one of subset of the group based on the comparison and determined sampling characteristic.

Another embodiment is a system for predicting the accuracy of DNA base identifications. This embodiment includes a predicted identity input component configured to receive a plurality of predicted DNA base identifications associated with a training data set; a subset generator configured to define a group of subsets; an identity comparison component configured to compare the predicted DNA base identifications with actual DNA base identifications for training data within each subset of the group; a sampling determination component configured to determine a sampling characteristic for each subset of the group based on training data within the respective subset; and a quality characterization determination component configured to determine a quality characterization for predicted DNA base identifications within at least one of subset of the group based on the comparison and determined sampling characteristic.

Yet another embodiment is a system for predicting the accuracy of DNA base identifications that includes means for receiving a training data set, the training data set comprising a plurality of predicted DNA base identifications; means for defining a group of subsets; means for comparing the predicted DNA base identifications with actual DNA base identifications for training data within each subset of the group; means for determining a sampling characteristic for each subset of the group based on training data within the respective subset; and means for determining quality characterization for predicted DNA base identifications within at least one of subset of the group based on the comparison and determined sampling characteristic.

One other embodiment is a storage device comprising instructions that when executed perform a method of receiving a training data set, the training data set comprising a plurality of predicted DNA base identifications; defining a group of subsets; comparing the predicted DNA base identifications with actual DNA base identifications for training data within each subset of the group; determining a sampling characteristic for each subset of the group based on training data within the respective subset; and determining quality characterization for predicted DNA base identifications within at least one of subset of the group based on the comparison and determined sampling characteristic.

DETAILED DESCRIPTION OF THE PREFERRED EMBODIMENT

Figure 1:
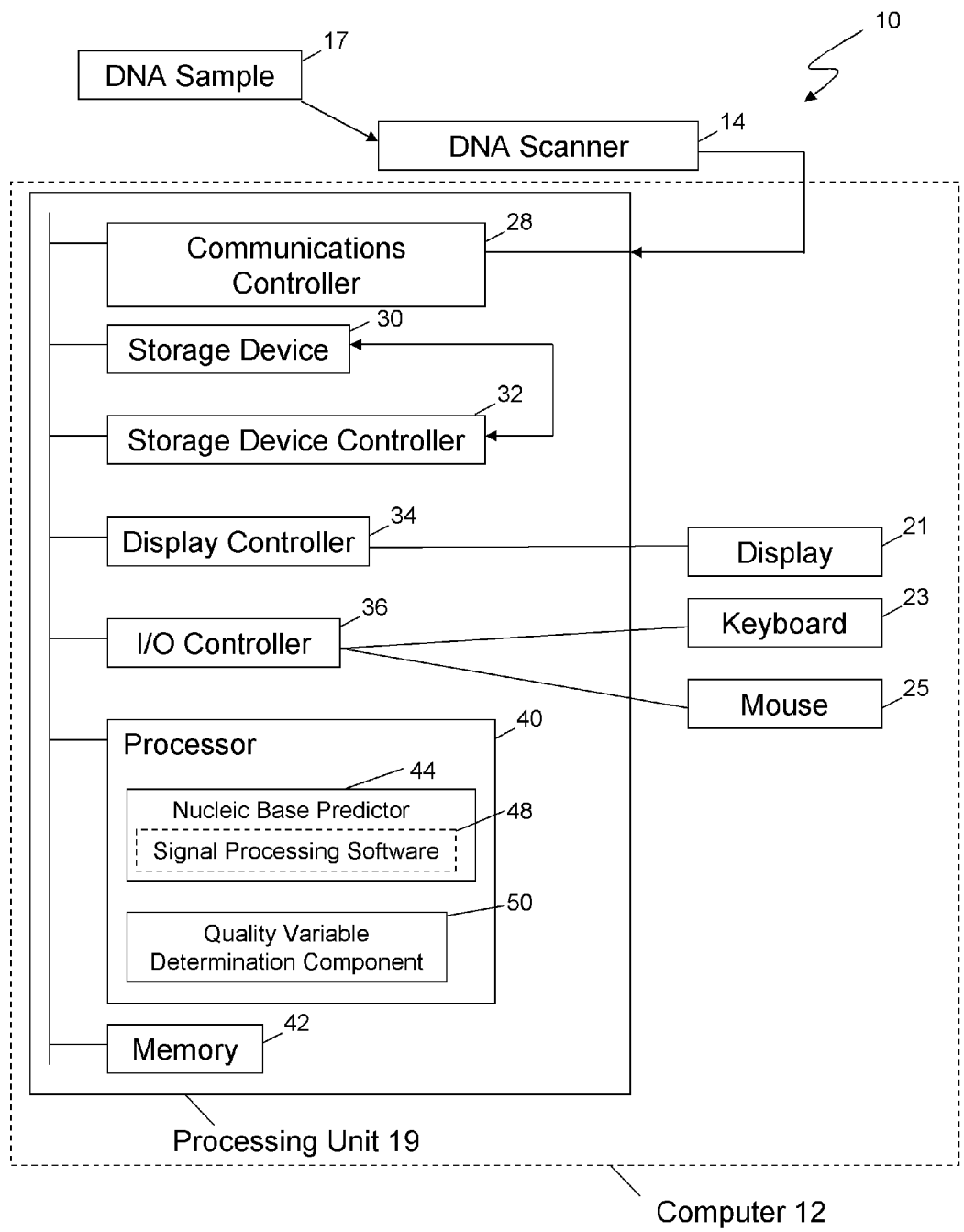
FIG. 1 shows a quality variable determination computer system.

Embodiments of the invention relate to systems and methods for increasing the accuracy of determining the sequence of a polynucleotide. In typical systems, each nucleotide base in a polynucleotide is uniquely labeled. In some embodiments, the labels are fluorescent. Once the nucleotides are labeled, the identity of each nucleotide base in the polynucleotide is determined in a process known as "base calling" or "base predicting". Frequently, electrophoresis is used such that DNA fragments pass through a scanner. During this process, the scanner determines the wavelength of light emitted by the fluorescent label on each base. As a base tagged with, for example, a first label passes through the scanner, a transient peak at the associated frequency will occur. If the next base is tagged with a different label, a transient peak at another frequency will occur. The signal may be separated into a plurality of signals (e.g., based on frequencies of the signal) corresponding to the different dyes.

In other embodiments, labeled nucleotides are detected on polynucleotides located on a surface, which can be imaged by a scanner. For example, different nucleotides can be labeled with different labels that are detected in separate images, such as maps of fluorescence intensity. In this embodiment, a set of intensities associated with a particular location or polynucleotide can be considered to comprise the "peak" as used herein. Such peaks can be further compared between multiple images, representing different nucleotides, to obtain a base call. A linked computer thereafter analyzes the scanner data or images to identify each nucleotide base in the polynucleotide. The analysis can also utilize sequence context information when making base calls.

Alternative methods that eliminate the separation step during electrophoresis have also been used. Many of these methods rely upon the technique of base extension and have been described for example in WO 93/21340, U.S. Pat. Nos. 5,302, 509 and 5,547,839. In these methods, templates or primers are immobilized on a solid surface before exposure to reagents for sequencing. The immobilized molecules are incubated in the presence of nucleotide analogues that have been modified to block addition of a hydroxyl group. The incorporation of such modified nucleotides by a polymerase ensures that only one nucleotide is added during each cycle of base extension. The added base is then detected through a label that is attached to the blocking group. Following detection, the blocking group is cleaved, and the process repeats for another round of base determination. By utilizing this technique, long stretches of DNA can be sequenced.

As described in further detail below, various characteristics of the label signal from a nucleotide may serve as useful indicators of the reliability of identifying the base that is attached to that label. For example, if a signal associated with a first fluorescent dye includes a sharp, large peak while the other signals include very shallow signals at a corresponding location, then the base associated with the first dye can be identified with a high reliability. However, if the signal associated with the first dye is shallower, or has a broader peak, and if signals associated with the other dyes also have substantial intensities, then the base identification of that dye may be more difficult and be considered less reliable.

Training data sets may be used to determine what type of signal characteristics produce reliable and unreliable base identifications. Various methods and systems disclosed herein assign values for quality variables (or sometimes "quality scores" or "confidence measures") to each base determination. These quality variables quantitate the reliability of specific parameter characteristics. The quality variables are calculated using a large number of base predications based on training data, wherein the characteristics and identity of each base is known. Thus, a relationship between the parameter characteristics and the base identity is determined for a variety of parameter characteristics. Quality variables depending on both the base identification accuracy and sampling characteristics of training data are thereby produced. By analyzing a number of subsets, each characterized by different parameter values, a process relating parameter characteristics to the quality variable (e.g., a look-up table) may be determined.

FIG. 1 shows a quality variable determination computer system 10, which may be configured to perform one or more method steps disclosed herein and may comprise one or more of the components of a system disclosed herein. The system is comprised of various modules as discussed in detail below. As can be appreciated by one of ordinary skill in the art, each of the modules comprises various sub-routines, procedures, definitional statements and macros. Each of the modules are typically separately compiled and linked into a single executable program. Therefore, the following description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

The system may be used in connection with various operating systems such as LINUX, UNIX or MICROSOFT WINDOWS®.

The system may be written in any conventional programming language such as C, C++, BASIC, Pascal, Python, Java, or FORTRAN and run under a conventional operating system. C, C++, BASIC, Pascal, Python, Java, and FORTRAN are industry standard programming languages for which many commercial compilers can be used to create executable code.

The invention is operational with numerous other general purpose or special purpose computing system environments or configurations. Examples of well known computing systems, environments, and/or configurations that may be suitable for use with the invention include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like.

A computer 12 may receive information from, for example, a DNA scanner 14 that reads a sequencing chip that has a treated DNA sample 17, such as one or more short lengths (or "fragments") of DNA. In some embodiments, the computer 12 receives information from a sequencing gel reader (not shown). The DNA scanner 14 may thus provide, for example, electropherogram data to the computer 12. Alternatively, raw data may be provided in the form of analog or digital signal, trace, or other numerical parameters, such as a stream or file of intensity values generated by the sequencing reaction, as well as various feature parameters derived from such data. A common data file format is Standard Chromatography Format (SCF), although other formats can be used. The computer 12 may comprise a processing unit 19, display device 21, and one or more input devices.

As used herein, an input device can be, for example, a keyboard 23, or mouse 25. The input device can also be a touch screen associated with the display, in which case the user responds to prompts on the display by touching the screen. The user may enter textual information through the input device such as the keyboard or the touch-screen.

A web browser comprising a web browser user interface may be used to display information (such as textual and graphical information) to a user. The web browser may comprise any type of visual display capable of displaying information received via a network. Examples of web browsers include Microsoft's Internet Explorer browser, Netscape's Navigator browser, Mozilla's Firefox browser, Apple's Safari browser, or any other browsing or other application software capable of communicating with a network.

The processing unit 19 may comprise a communications controller 28, a storage device 30, a storage device controller 32, a display controller 34, an I/O controller 36, a processor 40, and/or a memory 42.

Associated with, and in communication with the processor 40 may be a nucleic base predictor module 44 that is configured to predict the nucleotide sequence of a nucleic acid molecule. For example, the signals detected by the DNA scanner 14 input via the communications controller 28 may be analyzed (e.g., by a signal processing software 48) to predict the nucleotide sequence. The prediction may include pre-processing, such as downsampling of the data (e.g., as much as to 1 Hz if necessary), primer data removal, baseline adjustment, noise filtering, multicomponent transformation, dye mobility shift correction, and/or signal normalization. See, e.g., M. C. Giddings, et al., "A Software System For Data Analysis In Automated DNA Sequencing", Genome Research, vol. 8, pp. 644-665 (1998), which is hereby incorporated by reference in its entirety.

Processing the raw data can produce analyzed electropherograms or other data files with clearly defined peak information. The analyzed data in the form of electropherograms can then be processed using a base calling system, method or program, which can predict a sequence of bases in the DNA fragment. This sequence of bases is also referred to as a read and is usually about 1,000 bases long. One method for predicting DNA bases and assigning quality scores comprises Phred, as described in Ewing et al., Genome Research 1998 8: 175-185 and Ewing and Green, Genome Research, 1998 8: 186-194, both of which are hereby incorporated by reference in their entireties. The Phred algorithm as originally described can be used to predict the probability of an event, given a set of predictor values derived from data. Another method is described in U.S. Pat. No. 6,681,186, which is hereby incorporated by reference in its entirety. Not all of the information from called bases is used in subsequent processing to obtain or evaluate nucleotide sequence. In some instances, it is desirable to identify called bases that are associated with a low error or high reliability, quality or accuracy measure.

The processor 40 may also comprise a quality variable determination module 50 that is configured to determine a quality variable associated with each base prediction. A quality variable may comprise, for example, an error variable, a confidence variable, a reliability variable, an accuracy variable, a look-up table, and/or an accuracy prediction variable. As described in further detail below, in some instances, the quality variable is determined based on training data and may—for example—determine a quality variable based on parameters, identification accuracies and samplings of training data subsets. In such instances, the module 50 may determine a quality variable look-up table. In other instances, the quality variable determination module 50 determines a quality variable for non-training data based on, for example, a determination scheme (e.g., a look-up table) previously determined by the component. The quality variable may be based at least partly on one or more parameter values, as described in greater detail below.

In some instances, a quality variable (e.g., a quality variable value or quality variable look-up table) determined by the quality variable determination component 50 is output or stored (e.g., on storage device 30 or using memory 42). The quality variable may be output, for example, via a physical or virtual connection (e.g., over a network), a display 21, or a printer.

The processor 40 may comprise a microprocessor. The microprocessor may be any conventional general purpose single- or multi-chip microprocessor such as a Pentium® processor made by Intel Corporation. In addition, the microprocessor may comprise any conventional special purpose microprocessor such as a digital signal processor or a graphics processor. The microprocessor typically has conventional address lines, conventional data lines, and one or more conventional control lines.

The memory 42 may be any random access memory (RAM) or other readable and writeable memory device. The processor 40 may execute the software that implements a method disclosed herein and may utilize the memory 42. The processor 40 may comprise components of a system disclosed herein, such as the signal processor 48, the nucleic base predictor 44 and/or the quality variable determination module 50. Information, including software that implements a method disclosed herein, DNA sample files, etc. may be read from and written to the storage device 30, which may be coupled to the storage device controller 32. The storage device 30 may comprise a hard disk drive, a readable and writeable compact disc (CDRW) drive, a floppy disk drive, etc, including such devices connected to a network hub or server. The storage device 30 may comprise a device by which a machine may read from a machine readable medium such as the devices already mentioned, as well as, but not limited to, a stick or card memory device, a digital audio tape (DAT) reader, etc. In one embodiment, the storage device 30 comprises a plurality of disk drives comprising a disk array or other configuration. The processor 40 may communicate instructions to the display controller 34 to display images on the display device 21. The display controller 34 may be any display controller, and display device 21 may be any display monitor, including, but not limited to, a cathode ray tube (CRT) display monitor and a thin film transistor (TFT) or other LCD display screen.

In some embodiments, information (e.g., array data) may be transmitted between components of a system disclosed herein directly or via, for example, the communication controller 28 and/or over a computer network. A Local Area Network (LAN) or Wide Area Network (WAN) may be a corporate computing network, including access to the Internet, to which computers and computing devices comprising the system are connected. In one embodiment, the LAN conforms to the Transmission Control Protocol/Internet Protocol (TCP/IP) industry standard. In some instances, the information (e.g., training data parameters or identity predictions) is input to a system disclosed herein via the input device. In some instances, the information is received by loading the information, e.g., from a storage device 30.

The invention disclosed herein may be implemented as a method, apparatus, system or article of manufacture using standard programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

Figure 2:
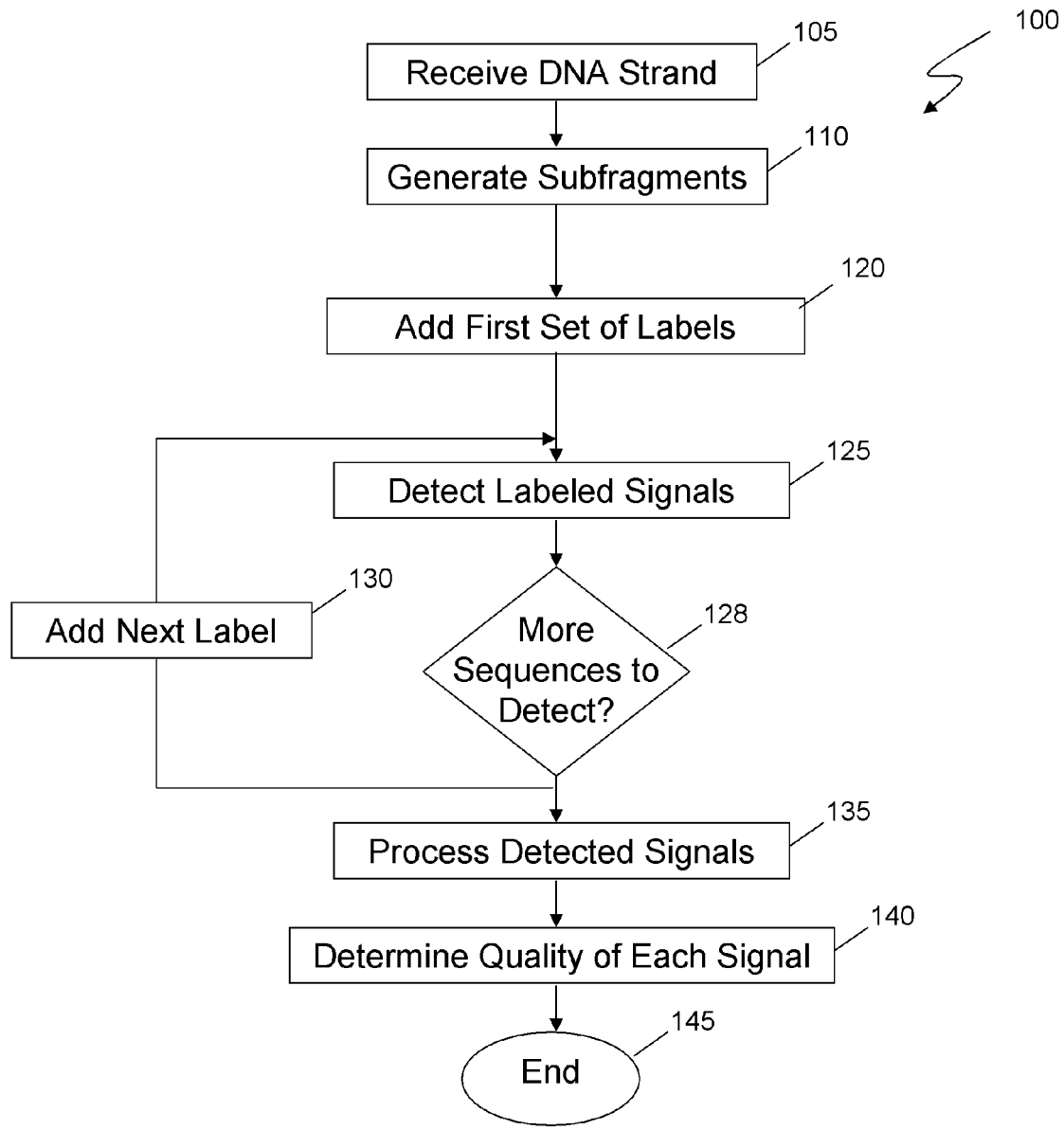
FIG. 2 shows a process for sequencing DNA.

FIG. 2 shows a process 100 for determining the nucleic acid sequence of a DNA molecule. At step 105, a DNA sample is received. In one embodiment, the DNA samples are received from an organism that is being genotyped. In another embodiment, the DNA sample is received as part of a determination of the genome of a particular organism. Once the process 100 has received a DNA sample, the process 100 moves to step 110, where sub-fragments of the received DNA sample are generated. The subfragments are then labeled at a state 120 so that they are detectable at a later stage of the method.

The process 100 moves to state 125 wherein the signals given off by each label are detected. A determination may be made at an optional process step 128 whether to detect more nucleotides, based, for example, on the quality of the signal or after a predetermined number of bases. If the DNA does have more nucleotides to be detected, then the chemistry for the next nucleotide determination is performed at a step 130. The process then returns to step 125 wherein the next nucleotide is detected.

If there are no additional nucleotides to detect at the decision state 128, the detecting portion of the process is completed. At any point after state 125, a state 135 is provided wherein the data gathered from each read up to that point is analyzed and stored. The signals detected from each nucleotide can be stored, for example, to the storage device 30. This provides a series of time-based images. After any state 135, a state 140 is also provided wherein a quality determination for each detected nucleotide is determined. The process 100 then terminates at an end state 145.

Figure 3:
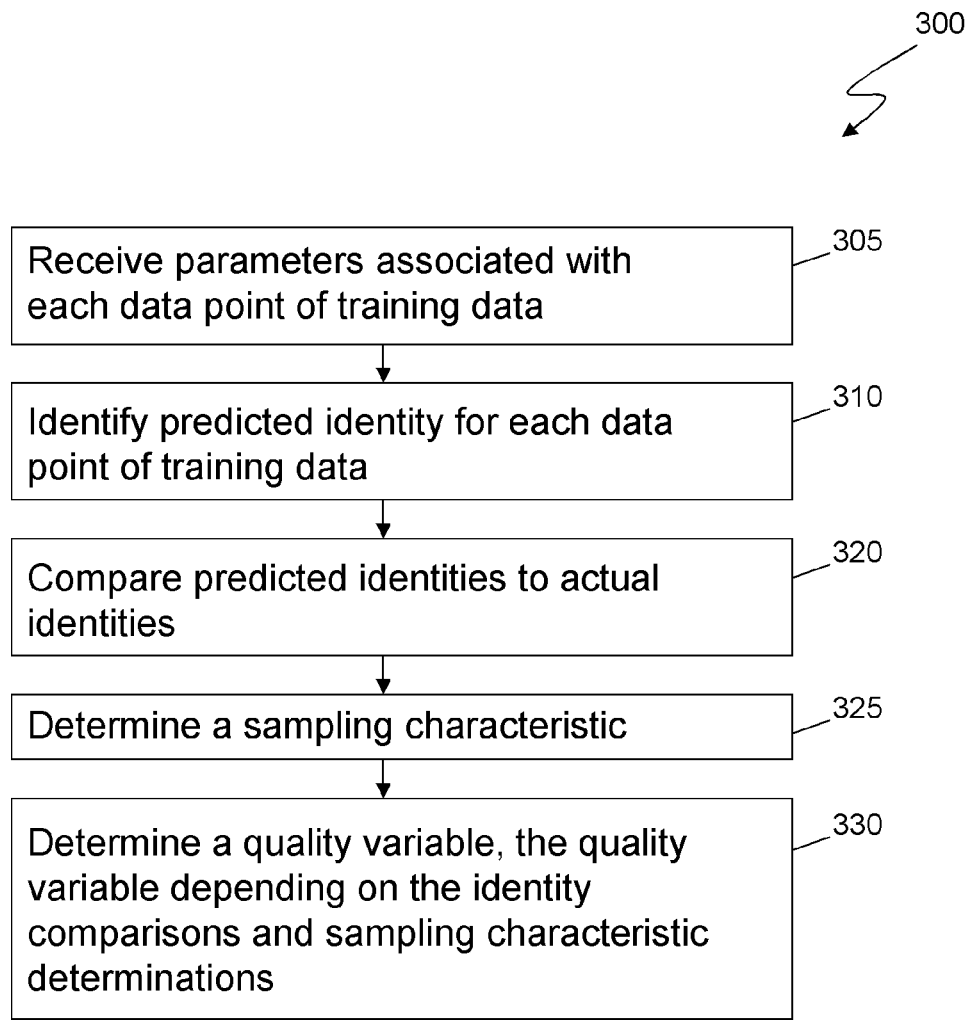
FIG. 3 shows a process for determining a quality variable associated with a DNA base identification for a training data set.
Figure 4:
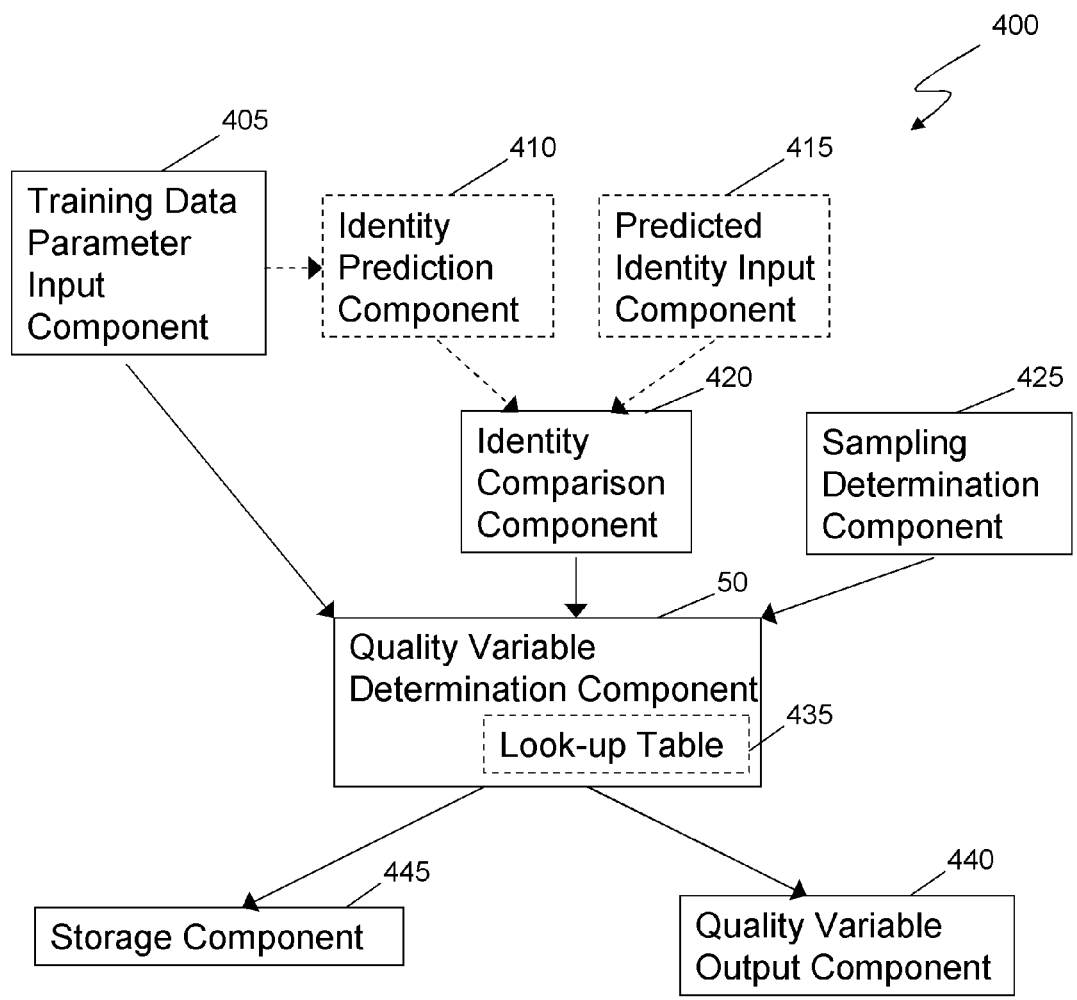
FIG. 4 shows a system for determining a quality variable associated with a DNA base identification for a training data set.

FIG. 3 shows a process 300 for determining a quality variable associated with a DNA base identification for a training data set, and FIG. 4 shows a system 400 for determining a quality variable associated with a DNA base identification for a training data set. In some embodiments, the quality variable determination component 50 of processor 40 of system 10 comprises part or all of the system 400 and/or is configured to perform part or all of the steps of process 300. In some instances, input components (e.g., training data parameter input component 405, identity prediction component 410 and/or predicted identity input component 415) may be sent to the system through the I/O controller 36 or communications controller 28 of system 10.

At step 305 of FIG. 3, parameters associated with data points of a training data set are received (e.g., by the training data parameter input component 405). The parameters may characterize peaks of a trace, such as from a DNA scanner 14. In some instances, one or more parameters commonly associated with Phred are used as parameters. In some instances, one or more parameters described in U.S. Pat. No. 6,681,186 are used as parameters. The parameters may comprise an apparent characteristic or a physical, real characteristic of a peak. The parameters may comprise or relate to, for example, peak height, peak width, peak location, relative peak locations, or ratios or differences thereof. The parameters may also relate to the properties of a hypothetical or idealized peak (such as a Gaussian or other mathematical distribution) extrapolated from a finite set of empirically derived parameters, for example predicted peak height, width or location. In one instance, the parameters comprise one or more of a peak height ratio for a current peak based on a first plurality of peaks (e.g., neighboring or adjacent peaks centered at a current peak); a second peak height ratio for the current peak based on a second plurality of peaks (e.g., centered at the current peak); a peak spacing ratio for the current peak (e.g., based on a largest peak spacing and a smallest peak spacing of the second plurality of peaks centered at the current peak) and a peak resolution. The parameters may comprise intrinsic peak characteristics. Parameters may relate to peak truncation, the intrinsic height of the peak and/or the intrinsic signal of other peaks at the candidate peak's position. In some instances, a plurality of parameters is associated with each data point (e.g., candidate peak or DNA base) from the training data set. The plurality of parameters may comprise, for example, at least about 2, 3, 4, 5, 6, 7, 8, 9 or 10 parameters. In some instances, the plurality of parameters comprise no more than about 2, 3, 4, 5, 6, 7, 8, 9 or 10 parameters. In some instances, the plurality of parameters comprise about 2, 3, 4, 5, 6, 7, 8, 9 or 10 parameters. In some embodiments, the parameters are determined at step 305 by a parameter determination component. In some embodiments, process 300 does not include step 305 and/or system 400 does not include component 405.

At step 310, predicted identities are identified for each data point of the training data. The predicted identities may comprise, for example, a predicted nucleic acid or DNA base. For example, for each peak read by the DNA scanner, a DNA base may be predicted to be associated with the peak (e.g., based on fluorescence associated with each of a plurality of nucleic acid-specific dyes). In some instances, the identities are predicted by an identity prediction component 410. The identity prediction component 410 may, for example, receive parameters from the training data input component 405 and determine identity predictions from any appropriate method, such as, for example, Phred or that described in U.S. Pat. No. 6,681,186. In other instances, the predicted identities are received as input by predicted identity input component 415.

At step 320, the predicted identities are compared to actual identities (e.g., by identity comparison component 420). In some instances, the predicted and actual identities are compared for a subset of the training data set or for a plurality of subsets. The comparison may comprise determining an identity comparison value, such as an error variable, an accuracy variable, and/or a reliability variable. (Notably, an identity comparison value includes variables that were, in some prior references, such as U.S. Pat. No. 6,681,186, termed "quality variables," when such variables do not depend on a sampling characteristic.) The identity comparison variable may be equal to a value QV defined as:

$$QV_{i,j,k,l} = -10 \cdot \log_{10} P, \qquad \text{Eqn. 1}$$

where P is the probability of error in the identity prediction. P may be defined as:

$$P = \frac{\delta_{i,j,k,l} + err_{i,j,k,l}}{\delta_{i,j,k,l} + err_{i,j,k,l} + corr_{i,j,k,l}}, \qquad \text{Eqn. 2}$$

where $err_{i,j,k,l}$ and $corr_{i,j,k,l}$ are the total number of erroneous and correct predicted identities for a subset defined with parameter set (i, j, k, l). For a particular training set, $\delta_{i,j,k,l}$ can be selected to be 0 or 1 for the duration of the training process. (While four parameter indices are shown here, the equation may be modified by increasing or decreasing the number of parameter indices.) In some instances, low numerical values of the quality variable are intended to indicate more accurate predictions.

At step 325, a sampling characteristic is determined (e.g., by sampling determination component 425). In some instances, the sampling characteristic is determined for a subset of the training data set or for a plurality of subsets. The sampling characteristic may comprise or relate to, for example, a number or fraction of data points used for the predicted-actual identity comparison. The sampling characteristic may relate a number or fraction of data points used for the predicted-actual identity comparison to a threshold value. The sampling characteristic may comprise a confidence characteristic or value.

One skilled in the art will appreciate that as the amount of available data increases, the width of a confidence interval can decrease, leading to a more precise estimate of error. This further allows regions of lower error probability to be identified and selected. In certain cases, however, low error probability may be assigned to regions due to relatively sparse data for that region. In the present invention, a confidence characteristic can be used to provide a more accurate prediction of the probability of a correct base call.

In one instance, the confidence characteristic comprises a binomial proportion confidence interval such as a normal approximation interval, a Wilson score interval, or a Clopper-Pearson interval. The normal approximation interval and Wilson score interval may be represented as $$\left\{\theta \;\middle|\; Z_{\alpha/2} \leq \frac{\hat{p}-\theta}{\sqrt{\hat{p}(1-\hat{p})/n}} \leq Z_{1-\alpha/2}\right\}$$

$$\left\{\theta \;\middle|\; Z_{\alpha/2} \leq \frac{\hat{p}-\theta}{\sqrt{\theta(1-\theta)/n}} \leq Z_{1-\alpha/2}\right\}$$

respectively. The Clopper-Pearson interval can be given as $$\{\theta | P[Bin(n;\theta) \leq X] \geq \alpha/2\} \cap \{\theta | P[Bin(n;\theta) \geq X] \geq \alpha/2\}$$

where X is the number of successes observed in the sample and Bin(n;θ) is a binomial random variable with n trials and probability of success θ. The interval can be calculated to correspond to a confidence of greater than 50%, 60%, 70%, 80%, 90%, 95%, 99%, 99.5%, or 99.9%. Other intervals can be used, such as those based on taking a number of standard deviations from the mean (or multiples or fractions thereof).

At step 330, a quality variable is determined (e.g., by quality variable process determination component 430), the quality variable depending on the identity comparison from step 320 and the sampling characteristic from step 325. In some embodiments, the quality variable is determined based on an identity comparison value and a sampling characteristic value. For example, the quality variable may be equal to an identity comparison value plus or minus an associated sampling characteristic value. As described in further detail below, basing the quality variable at least partly on the sampling characteristic value may improve the accuracy of the quality variable. In some instances, the quality variable determination component 430 generates a look-up table 435. The look-up table may comprise a plurality of quality variables. In some instances, the look-up table associates one or more parameter values with a quality variable, as described in further detail below. The quality variable or look-up table 435 may then be used to predict an accuracy or quality of a base identification based on non-training data (e.g., by using associated parameter values). See, for example, the description of process 700 and the system 800 below. As indicated above with respect to system 10, the quality variable may be output (e.g., via a display or printer or transmitter) or stored (via a storage device or memory).

Figure 5:
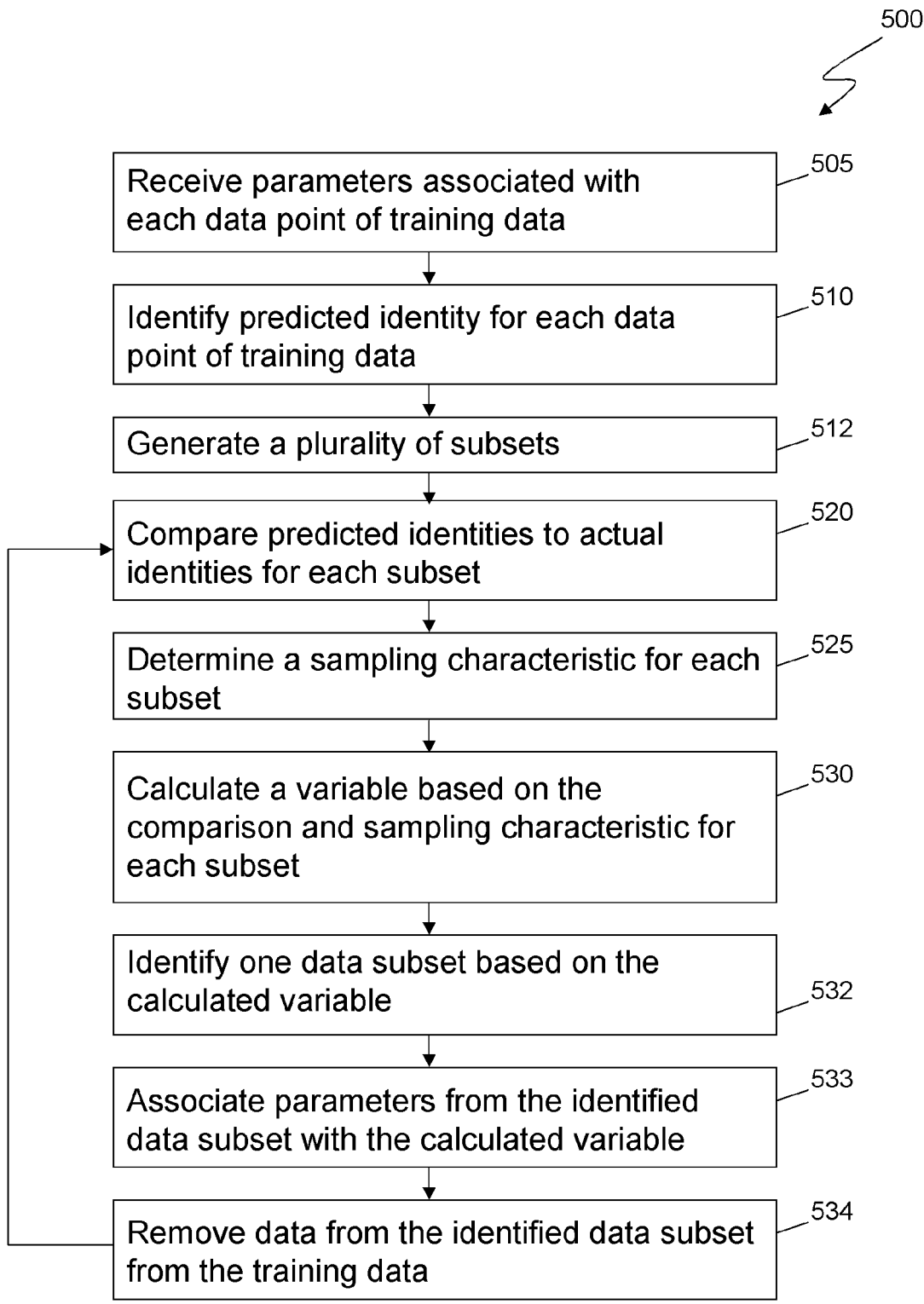
FIG. 5 shows an iterative process for determining a quality variable associated with a DNA base identification for a training data set.
Figure 6:
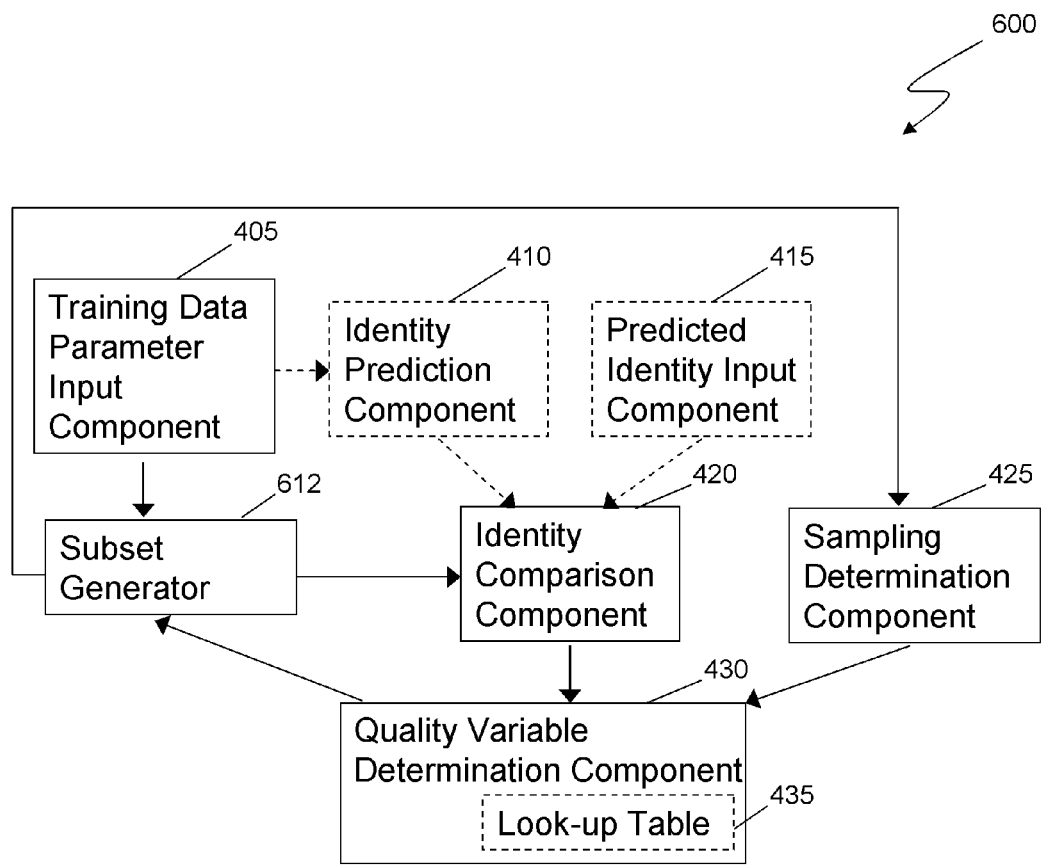
FIG. 6 shows a system for iteratively determining a quality variable associated with a DNA base identification for a training data set.

FIG. 5 shows an iterative process 500 for determining a quality variable associated with a DNA base identification for a training data set, and FIG. 6 shows a system 600 for iteratively determining a quality variable associated with a DNA base identification for a training data set. In some embodiments, the quality variable determination component 50 of processor 40 of system 10 comprises part or all of the system 600 and/or is configured to perform part or all of the steps of process 500. In some instances, input components (e.g., training data parameter input component 405, identity prediction component 410 and/or predicted identity input component 415) may use the I/O controller 36 or communications controller 28 of system 10.

At step 505 of process 500, parameters associated with each data point of training data are received. At step 510, predicted identities for each data point of training data are identified. Additional details and embodiments related to these process steps are described with respect to steps 305 and 310 of process 300.

At step 512, a plurality of subsets is generated (e.g., by subset generator 612—FIG. 6). The subsets may be generated based on the parameters. For example, a bin may be described by a set of parameter thresholds. In one instance, the one or more parameter values may be partitioned into a plurality of bins. Bins may be defined by any appropriate method, such as methods described in U.S. Pat. No. 6,681,186. The subset generator 612 may be configured to determine criteria for subset definitions and/or for identifying a portion of a data set (e.g., a training data set) which is within the subset as defined. In some instances, one or more parameter thresholds are received (e.g., from a user). In some instances, one or more parameter thresholds are automatically generated (e.g., by a computer).

At step 520, the predicted identities are compared to the actual identities for each subset, and at step 525, a sampling characteristic is determined for each subset. Additional details and embodiments related to these process steps are described with respect to steps 320 and 325 of process 300.

At step 530, a variable is calculated based on the comparison and sampling characteristic. The variable may relate to the probability that a prediction of the identity of a non-training data point within the subset is accurate. The variable may be stated as an accuracy value or characterization equal to 100% decreased by an error value E. The variable may be, for example, an accuracy variable is further decreased by a confidence variable C to provide an even more conservative accuracy value. Thus, in one embodiment, the accuracy characterization can be stated in percentage terms as a value equal to 100%-E-C. In other embodiments, the confidence variable defines a confidence interval for the accuracy variable, so that the upper or lower value of the interval (or fractional intermediate value thereof) is used as the calculated variable.

At step 532, one data subset is identified based on the calculated variable. The identified subset may comprise, for example, the subset with the highest or lowest calculated variable. In some instances, the identified subset comprises the subset with a calculated variable indicating the highest accuracy or reliability or lowest error among all of the subsets.

At step 533, parameters associated with the identified data subset are associated with the calculated variable. In one embodiment, subset-defining parameter criteria are associated with the calculated variable. For example, parameter thresholds of the subset may be identified.

At step 534, data from the identified data subset is removed from the training data. Therefore, all data points within the identified subset are removed from all subsets. In some instances, the identified subset is then removed from the plurality of subsets. The process then returns to step 520 and continues until all (or a predetermined subset of) data has been removed.

Steps 532, 533, 534 may be performed, for example, by the quality variable determination component 430.

Figure 7:
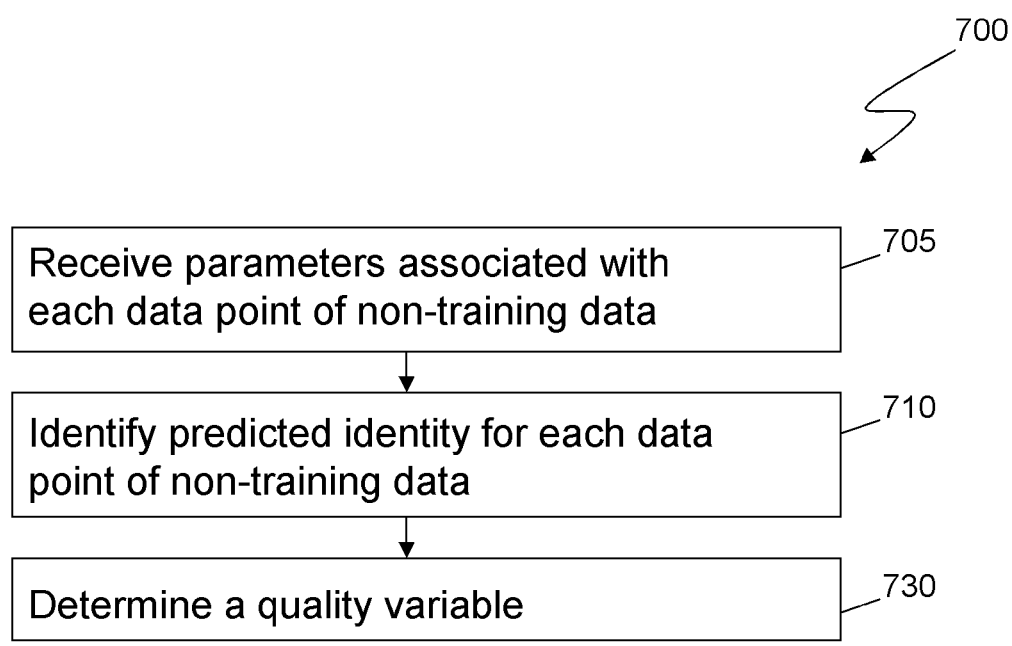
FIG. 7 shows a process for determining a quality variable associated with a DNA base identification for a non-training data set.
Figure 8:
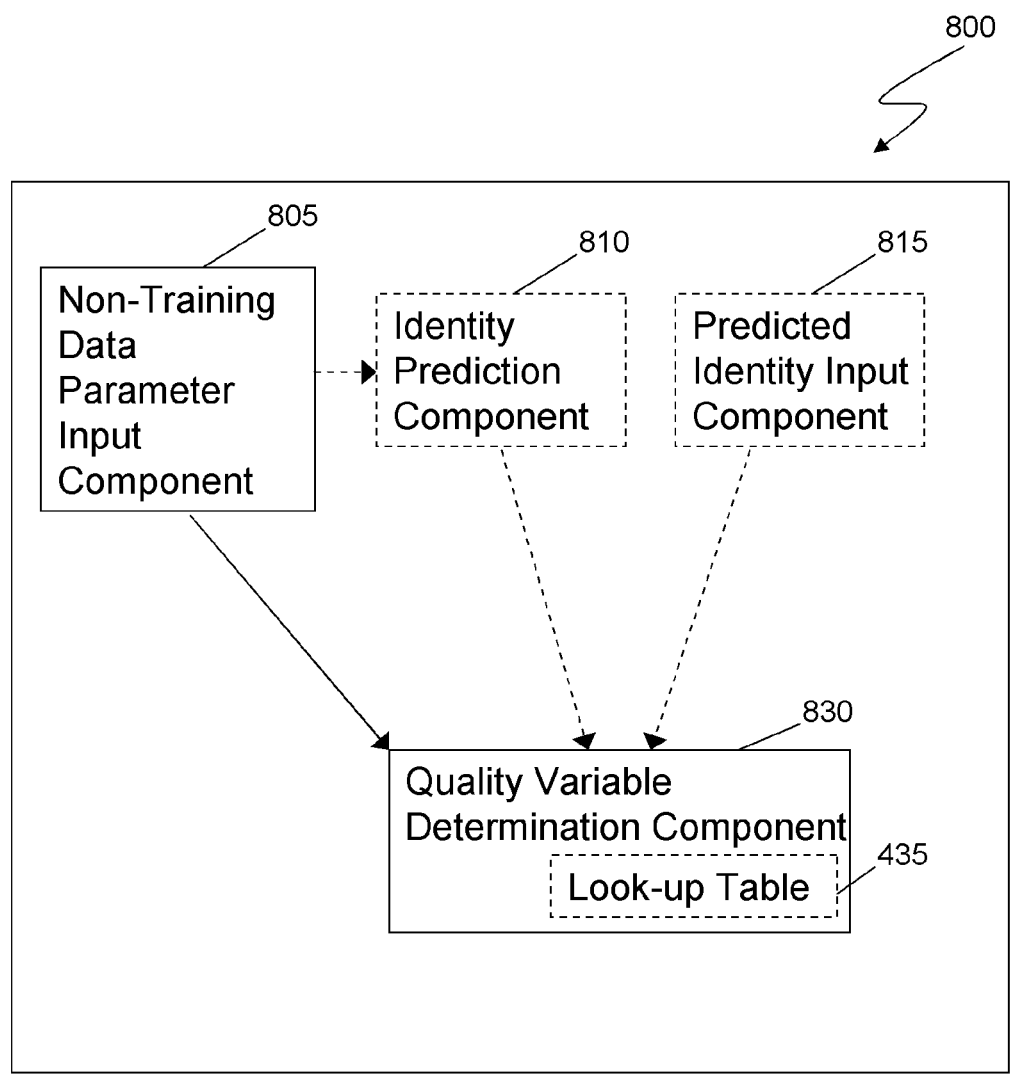
FIG. 8 shows a system for determining a quality variable associated with a DNA base identification for a non-training data set.

FIG. 7 shows a process 700 for determining values for a quality variable associated with DNA base identification for individual datapoints in a non-training data set, and FIG. 8 shows a system 800 for determining values for a quality variable associated with a DNA base identification for a non-training data set. In some embodiments, the quality variable determination component 50 of processor 40 of system 10 comprises part or all of the system 800 and/or is configured to perform part or all of the steps of process 700.

At step 705, parameters associated with data points of a non-training data set are received (e.g., by the training data parameter input component 805). The non-training data set may comprise, for example, data associated with DNA for which part or all of the sequence is unknown. The parameters may comprise parameters similar or equivalent to one, more than one or all of the parameters described for embodiments related to step 305 of process 300. For example, the parameters may comprise or relate to, for example, peak height, peak width, peak location, relative peak locations, or ratios or differences thereof. In one instance, the parameters comprise one or more of a peak height ratio for a current peak based on a first plurality of peaks (e.g., peaks centered at a current peak); a second peak height ratio for the current peak based on a second plurality of peaks (e.g., centered at the current peak); a peak spacing ratio for the current peak (e.g., based on a largest peak spacing and a smallest peak spacing of the second plurality of peaks centered at the current peak) and a peak resolution.

At step 710, predicted identities are identified for each data point of the non-training data. The predicted identities may comprise, for example, a predicted nucleic acid or DNA base. For example, for each point on an array or flow cell, a DNA base may be predicted to be associated with the peak (e.g., based on fluorescence associated with each of a plurality of nucleic acid-specific dyes). In some instances, the identities are predicted by an identity prediction component 810. The identity prediction component 810 may, for example, receive parameters from the non-training data input component 805 and determine identity predictions from any appropriate method, such as, for example, Phred or that described in U.S. Pat. No. 6,681,186. In other instances, the predicted identities are received as input by predicted identity input component 815. In some instances, the predicted identities are not identified or received, such that process 700 does not include step 710 and system 800 does not include either the identity prediction component 810 or the predicted identity input component 815.

At step 730, the value of a quality variable is determined (e.g., by the quality variable determination component 830). The quality variable may be of a type determined, for example, in step 330 of process 300, or in step 530 of process 500, as disclosed above. In some embodiments, process 300 or process 500 associates particular parameters with particular quality variables using training data, and at step 730, an appropriate quality variable is determined for data of a non-training data set based on one or more parameters associated with the data and a result (e.g., a result output or stored at step 330) of process 300 or 500. In one instance, a result of process 300 or 500 comprises look-up table 435. The look-up table 435 may comprise associate parameter values with quality variables. For example, the look-up table 435 may comprise a series of rows or a series of columns, each row or column including a parameter defining condition (e.g., a range of one or more parameters or one or more parameter thresholds) and a quality variable.

The quality variable determined by process 700 or system 800 may then be stored or output by, for example, the processing unit 40 of system 10. In some embodiments, a plurality of quality variables (e.g., quality variables associated with a plurality of potential bases of a sample) is stored or output. The plurality of variables may be stored or output, for example, with an associated plurality of predicted identifications, which may be obtained by any appropriate method, process, system or component disclosed herein. In some embodiments, a computer receives scanner data associated with a sample, determines a plurality of parameters associated with the scanner data, predicts the identity of a plurality of bases associated with the sample, determines a plurality of quality variables associated with the prediction, and outputs or stores one or both of the predicted identities and the quality variables. In some embodiments, a computer receives a plurality of parameters associated with scanner data of a sample, predicts the identity of a plurality of bases associated with the sample, determines a plurality of quality variables associated with the prediction, and outputs or stores one or both of the predicted identities and the quality variables.

In some embodiments, a computer-readable or machine-readable medium is provided having instructions stored thereon which, when executed by a processor, cause the machine to perform operations comprising one or more steps disclosed herein. As used herein, instructions refer to computer-implemented steps for processing information in the system. Instructions can be implemented in software, firmware or hardware and include any type of programmed step undertaken by components of the system.

EXAMPLE

A file of intensity values was received by a computer from a DNA scanner. A look-up table comprising quality variables was generated using the standard Phred method, as described in Ewing et al., Genome Research, 1998 8: 175-185 and Ewing and Green, Genome Research, 1998 8: 186-194. A second look-up table was generated, using a system and method, as disclosed herein. Particularly, instead of defining quality variables of data subsets as QV from Equation 1, the quality variable was calculated to be equal to the lower value of the calculated Clopper-Pearson interval (selecting a confidence level of 95%). Subsets with the most accurate quality variables were then associated with the corresponding quality variable in the second look-up table and removed from the data set. The process continued, as described in connection to FIGS. 5 and 6.

Quality variables associated with bases from six data sets were then determined using either the first or second look-up table. The quality variables were compared to actual quality variables and RMS (root-mean-square) errors of the predicted and actual variables were calculated and shown in Table 1. Quality variables predicted by using the second look-up table, associated with the modified quality variable, were more accurate (indicated by lower RMS errors) than those predicted by using the first look-up table, associated with the standard Phred method, demonstrating an increase in the quality and reliability of base prediction using the improved method of the invention. This method can be applied to any set of monotone predictors to predict the probability of an event more accurately.

TABLE 1

RMS Errors of Quality variables predicted using look-up tables generated using standard Phred or the Application Method.

| Data Set | RMS Error (Standard Phred) | RMS Error (Application Method) |
|---|---|---|
| 1 | 3.77 | 1.46 |
| 2 | 4.9 | 2.3 |
| 3 | 4.2 | 2.0 |
| 4 | 2.7 | 1.4 |
| 5 | 3.6 | 1.5 |
| 6 | 2.4 | 1.9 |

While the invention has been discussed in terms of certain embodiments, it should be appreciated that the invention is not so limited. The embodiments are explained herein by way of example, and there are numerous modifications, variations and other embodiments that may be employed that would still be within the scope of the present invention. Components can be added, removed, and/or rearranged. Additionally, processing steps may be added, removed, or reordered. A wide variety of designs and approaches are possible.

For purposes of this disclosure, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

What is claimed is:

1. A system for determining the quality of predicted DNA base identifications, the system comprising a processor configured to:
   receive a training data set, the training data set comprising a plurality of predicted DNA base identifications;
   define a group of subsets;
   compare the predicted DNA base identifications with actual DNA base identifications for training data within each subset of the group;
   determine a sampling characteristic for each subset of the group based on training data within the respective subset; and
   determine a quality characterization for predicted DNA base identifications within at least one of subset of the group based on the comparison and determined sampling characteristic;
   wherein the sampling characteristic comprises a confidence value comprising a binomial proportion confidence interval value; and
   detect nucleotides based on the quality characterization.

2. The system of claim 1, the processor further configured to receive parameter values associated with the training data set.

3. The system of claim 2, wherein define the group of subsets is based on the parameter values.

4. The system of claim 2, wherein define the group of subsets comprises partition the parameter values into a plurality of bins.

5. The system of claim 2, the processor further configured to determine the predicted DNA base identifications based on the received parameter values.

6. The system of claim 2, wherein the parameter values comprise at least one of
   a first peak height ratio for a current peak based on a first plurality of called peaks centered at a current peak;
   a second peak height ratio for the current peak based on a second plurality of called peaks centered at the current peak;
   a peak spacing ratio for the current peak based on a largest peak spacing; and
   a smallest peak spacing of the second plurality of called peaks centered at the current peak and a peak resolution.

7. The system of claim 1, the processor further configured to determine an accuracy of the base prediction based on the determined quality characterization.

8. The system of claim 7, wherein determine the accuracy of the base prediction comprises reference a look-up table.

9. The system of claim 1, wherein determine the quality characterization comprises generate an accuracy prediction look-up table.

10. The system of claim 9, wherein generate the look-up table comprises:
    define the plurality of subsets by partitioning parameter values associated with data of the training data set into a plurality of bins;
    populate the plurality of bins with the predicted DNA base identifications; iteratively performing the following process:
    compute a quality characterization for each subset of the group;
    select an extreme quality characteristic subset as the considered subset having the largest or smallest quality characteristic of the group;
    store the largest or smallest quality characteristic and corresponding threshold values in the look-up table; and
    adjust the quality characteristic for the group of considered subsets such that the quality characteristic no longer depends on data within the extreme quality characteristic subset.

11. The system of claim 10, the processor further configured to delete the extreme quality characteristic subset from the group.

12. The system of claim 10, the processor further configured to iteratively perform until all of the data from the training data set has been within at least one extreme characteristic subset.

13. The system of claim 1, the processor further configured to:
    determine a plurality of quality characterizations, each quality characterization being associated with at least one threshold parameter value; and
    store the quality characterizations and the corresponding threshold parameter values in a look-up table.

14. The system of claim 13, the processor further configured to:
    receive at least one parameter value associated with data of a non-training data set; and
    select a quality characterization from the look-up table, the selected quality characterization being that the at least one corresponding threshold parameter values exceed the at least one parameter value associated with data of the non-training data set.

15. The system of claim 1, wherein the compare comprises calculate an error value E.

16. The system of claim 1, wherein the training data set is received from a memory.

17. The system of claim 1, wherein the quality characterization is output via a physical or virtual connection, a display or a printer.

18. The system of claim 1, wherein the binomial proportion confidence interval value comprises a Clopper-Pearson interval value.

19. The system of claim 1, wherein the compare comprises calculate an error value E,
 wherein the sampling characteristic comprises a confidence value C, and wherein the quality characterization comprises a value equal to 100%-E-C.

\* \* \* \* \*